United States Patent [19]

Scott

[11] Patent Number: 4,686,969
[45] Date of Patent: Aug. 18, 1987

[54] KNEE BRACE HAVING UPPER CUFF WITH CROSSED STRAPS

[76] Inventor: Edwin R. Scott, 927 South 450 East, Orem, Utah 84057

[21] Appl. No.: 818,230

[22] Filed: Jan. 13, 1986

[51] Int. Cl.⁴ .............................................. A61F 3/00
[52] U.S. Cl. .................................................. 128/80 C
[58] Field of Search ................. 128/80 C, 80 F, 80 R, 128/88

[56] References Cited

U.S. PATENT DOCUMENTS

| | | | |
|---|---|---|---|
| 1,092,836 | 4/1914 | Hart | 128/80 C X |
| 1,622,211 | 3/1927 | Sheehan | 128/80 C X |
| 4,361,142 | 11/1982 | Lewis et al. | 128/80 C |
| 4,372,298 | 2/1983 | Lerman | 128/80 C |
| 4,487,200 | 12/1984 | Feanny et al. | 128/80 C |

Primary Examiner—Clifford D. Crowder

[57] ABSTRACT

A knee brace having a rigid lower cuff including a shell molded to the leg beneath the knee and a strap to encircle the leg and the shell and to immobolize the shell on the leg; an upper cuff including crossed, non-resilient straps to position anteriorly of the thigh and a strap to encircle the thigh and the crossed straps and a pair of hinges to extend along opposite sides of the knee and rigidly connected to the shell and having the crossed straps attached thereto.

6 Claims, 3 Drawing Figures

KNEE BRACE HAVING UPPER CUFF WITH CROSSED STRAPS

BRIEF DESCRIPTION OF THE INVENTION

1. Field of the Invention

This invention relates to knee braces and particularly to braces providing for hinge movement of the knee while at the same time providing for lateral and rotational stability of the knee joint.

2. Prior Art

The human knee is subjected to a lot of stress and strain and particularly, during running and jumping movements. Athletes, in particular, are very apt to incur a knee injury as a result of a blow to the knee or to a twisting of a knee. Such injuries are especially apt to occur during participation in contact sports.

A great many knee braces have been proposed in the past. These range from braces of the type that are intended to totally immobolize the knee to fully encompassing elastic bandages that are intended to provide for some flexibility, while limiting lateral movement of the components of the knee joint. Some of the braces known in the past have been intended for use either as a relatively permanent brace, intended for long-term wear or as a brace to be worn, for example, for rather short time periods and that are intended to serve as supports for weakened knees. The knee braces providing for pivoting of the knee are generally intended to prevent any unnatural movement of the knee joint which could injure knee ligaments. It is also a function of these braces to permit the normal swinging movement of the knee joint about a horizontal axis through the knee. This permits a normal walking or running motion. The known braces are intended to prevent sudden movement of upper and lower legs to one side or the other and to prevent twisting or rotation of the lower leg relative to the upper leg, about a vertical axis.

U.S. Pat. No. 4,372,298, discloses a knee brace that is intended to be worn by a post-operative patient who has had knee surgery, or by an athelete or the like, desiring support to prevent injuries to the knee area. Upper and lower curved support members are respectively adapted to be fitted around the back of the user's upper leg above the knee joint and the back of a patient's lower leg below the knee joint. The upper and lower support members are interconnected by hinges at each side of a user's leg and flexible straps are adapted to be wound around the upper and lower members, with the straps being wrapped in opposite directions to one another in an effort to prevent undesired twisting or rotation of the upper and lower legs. U.S. Pat. No. 4,503,846, discloses a knee brace having a lower cuff adapted to fit over the front of the user's leg, below the knee and an upper cuff, adapted to fit around the rear of the thigh, above the knee and with a pair of straps positioned between the cuffs and adapted to fit around the leg, above and below the knee, respectively.

The knee braces proposed in the past have employed rigid upper and lower cuffs to accomodate the hinge of the brace. In such braces, there is a tendency for the brace to angularly shift away from and then back against the user's leg as the knee flexes and extends. This shifting or "pistoning" action results in eventual slipping or migration of the brace towards the ankle.

OBJECTS OF THE INVENTION

Principal objects of the present invention are to provide a knee brace having a rigid, molded lower leg engaging member or cuff that will engage the anterior of the leg and cooperate with the tibia to provide an immobilized reaction member for the brace while also having a yieldable upper cuff that will accomodate normal knee bending.

Other objects are to provide a knee brace that is securely held in place on the leg; that is easily installed and removed; and that is light in weight.

FEATURES OF THE INVENTION

Principal features of the invention include a rigid, molded lower leg cuff that will engage and become immobolized with the tibia and a wide elasticized rubberized strap that will provide an inner cushion for the rigid member and wraps fully around the rigid member to immobolize the member with respect to the tibia.

Crossing straps are provided to fit across the front of the user's thigh, above the knee, and the crossing straps are connected to upper, extension arms, of hinge assemblies, the lower portions of which are rigidly affixed to the rigid member. A flexible pad, connected to one of the upper extensions is adapted to extend around the rear of the user's leg, above the knee and a wide, elasticized rubber strap, is connected to the other of the upper links, and is adapted to be attached to the flap and to extend fully around the crisscross straps and the flap, to properly position the crisscross straps above the knee. Another strap extends from one of the rigid hinge members around the leg, above the calf to be adjustably secured to the other rigid hinge member.

Other objects and features of the invention will become apparent from the following detailed description and drawing, disclosing what is presently contemplated as being the best mode of the invention.

THE DRAWING

In the drawing:

FIG. 1 is a perspective view of the brace, viewed from the leg side of the brace, and showing the brace ready for positioning on a leg;

FIG. 2, a similar view taken from the front, or outside, of the brace; and

FIG. 3, a perspective view of the brace as positioned on a leg, the leg being shown in phantom.

DETAILED DESCRIPTION

Figure 1:
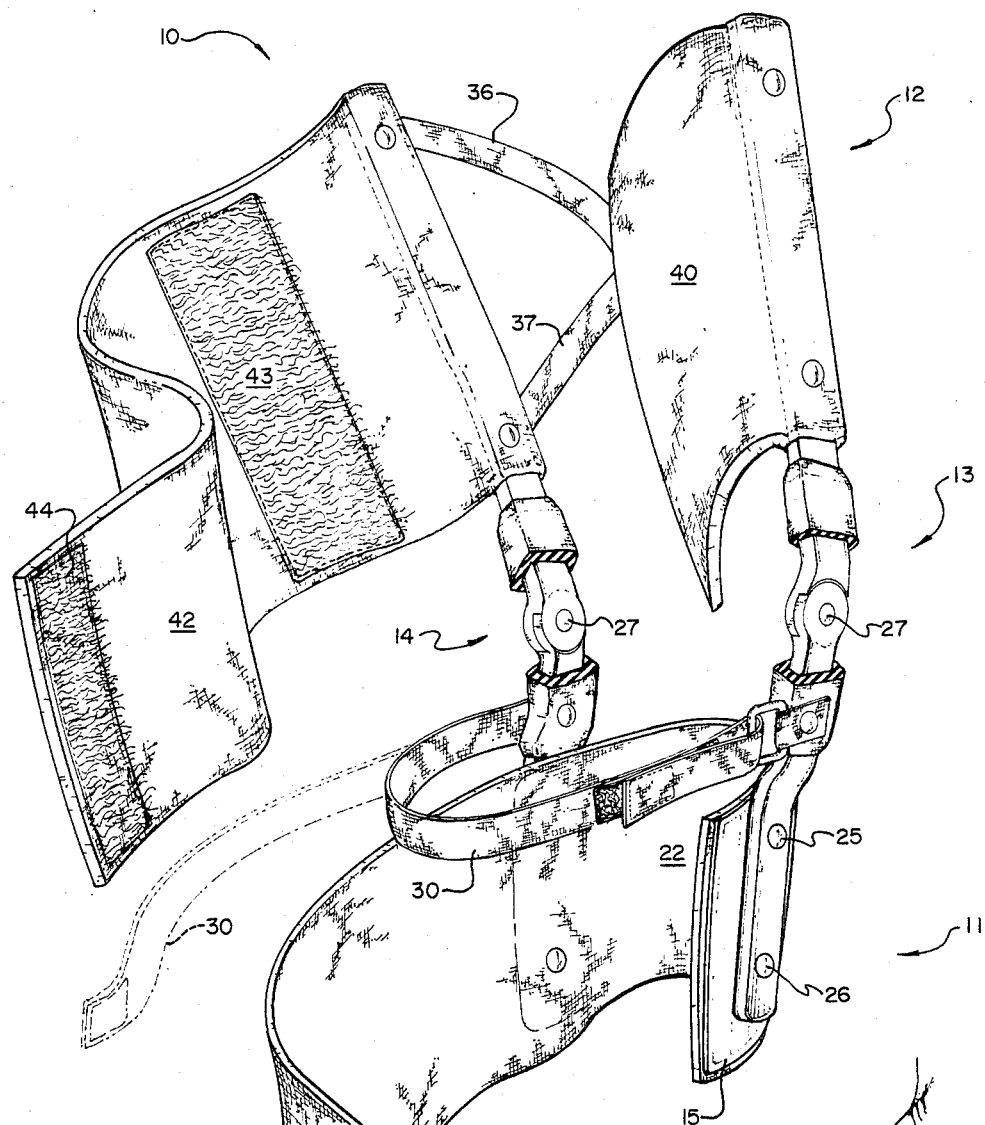

Referring now to the drawing:

In the illustrated preferred embodiment, the knee brace of the invention, shown generally at 10, includes a lower cuff 11 and an upper cuff 12 interconnected by pivot links 13 and 14.

The lower cuff 11 comprises a rigid shell 15, made of fiberglass, or other suitable materials, and molded to fit around the anterior portion of the lower leg, beneath the knee, of the user. The shell is made to extend from approximately two inches beneath the knee cap for a distance of between four and five inches. It has been found that if the width of the shell is less than about three inches it does not provide sufficient gripping action to provide the stabilization required for the brace. Also, it has been found that if the shell is over about six inches in width it becomes too uncomfortable for the user and adds, additional undesirable weight to the brace. A wide strap 22 fully covers the inside of shell 15 extends slightly beyond one end of the shell and above and below the top and bottom edges of the shell, respectively, and beyond the opposite edge thereof with sufficient length to allow the strap to be passed around the posterior of the lower leg and fully around the outside of the shell before being secured upon itself by means of hook fasteners 23, which may be "Velcro" fasteners of well known type. The hook fasteners engage with a napped back surface of the straps, the front surfaces of which are exposed rubberized material. The strap 22 is made stretchable so that it can be firmly wrapped around the user's leg and the rubberized material will hold the cuff against slippage up and down the leg.

Hinges 13 and 14 each have a lower extension arm 24 riveted at 25 and 26 to the shell 15 and projecting upwardly therefrom to be pivotally connected at 27 to upper extension arms 28 that project further upwardly to serve as components of the upper cuff 12.

Another strap 30 of flexible resilient material has one end 31 fixed to one lower extension arm 24 above shell 15 and another end 32 adapted to be turned through a D-ring 33 fixed to a free end 34 of a short strap 35, the other end of which is fixed to the other lower extension 24 above shell 15. The strap 30 is adapted to be passed posteriorly around the top of the calf muscle, just below the popileteal space of the user and is snugged up and secured by attached hook connectors 30a on the end of strip 30 to the strap itself.

Upper cuff 12, in addition to the upper arm extension 28, includes a pair of centrally crossing flexible straps 36 and 37 of non-resilient material. Each of the straps 36 and 37 has one end connected to an upper arm extension 28 adjacent to the top thereof and another end connected to the other upper arm extension intermediate the lengths of the arm extensions. The flexible straps 36 and 37 may be attached to the upper arm extensions by screws 38.

A protective flap 40 preferably made from the same material as strap 42 has one end fixed as by the screws 38 and is long enough to extend at least substantially around the posterior of the upper leg of the user.

Another wide strap 42, also preferably of the same material as strap 22, has a pair of pads 43 and 44 of hooked material and with pad 43 intermediate the length of the strap and pad 44 at a free end of the strap. The other end of strap 42 is attached to the other movable link 28 as by sewing it around the link and by attaching it with screws 38. The strap 42 is long enough to extend posteriorly around the upper thigh of a user when the crossed straps 36 and 37 are positioned anteriorly on the upper leg. Pad 43 engages and is locked to the napped back side of protective flap 40 and strap 42 then stretches fully around the leg and over straps 36 and 37 so that the pad 44 will lock on the napped surface of strap 42. It has been found that the width of the upper cuff, i.e. the distance between ends of straps 36 and 37 on an upper arm extension 28 and the width of the protective flap 40 and strap 42 must be at least four inches to insure proper anchoring of the cuff to the user's leg.

Figure 3:
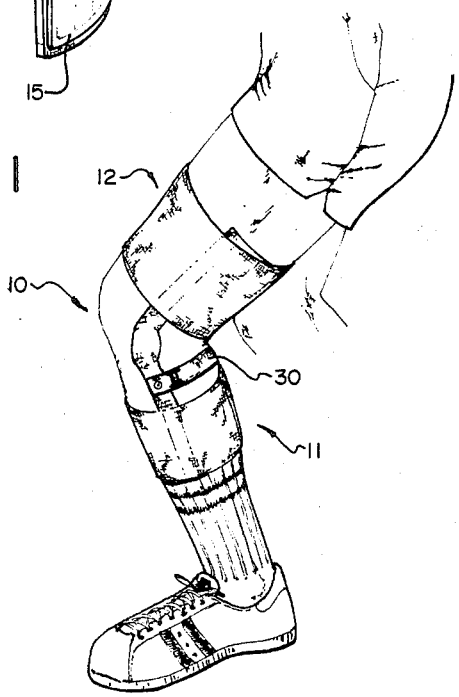
Figure 2:
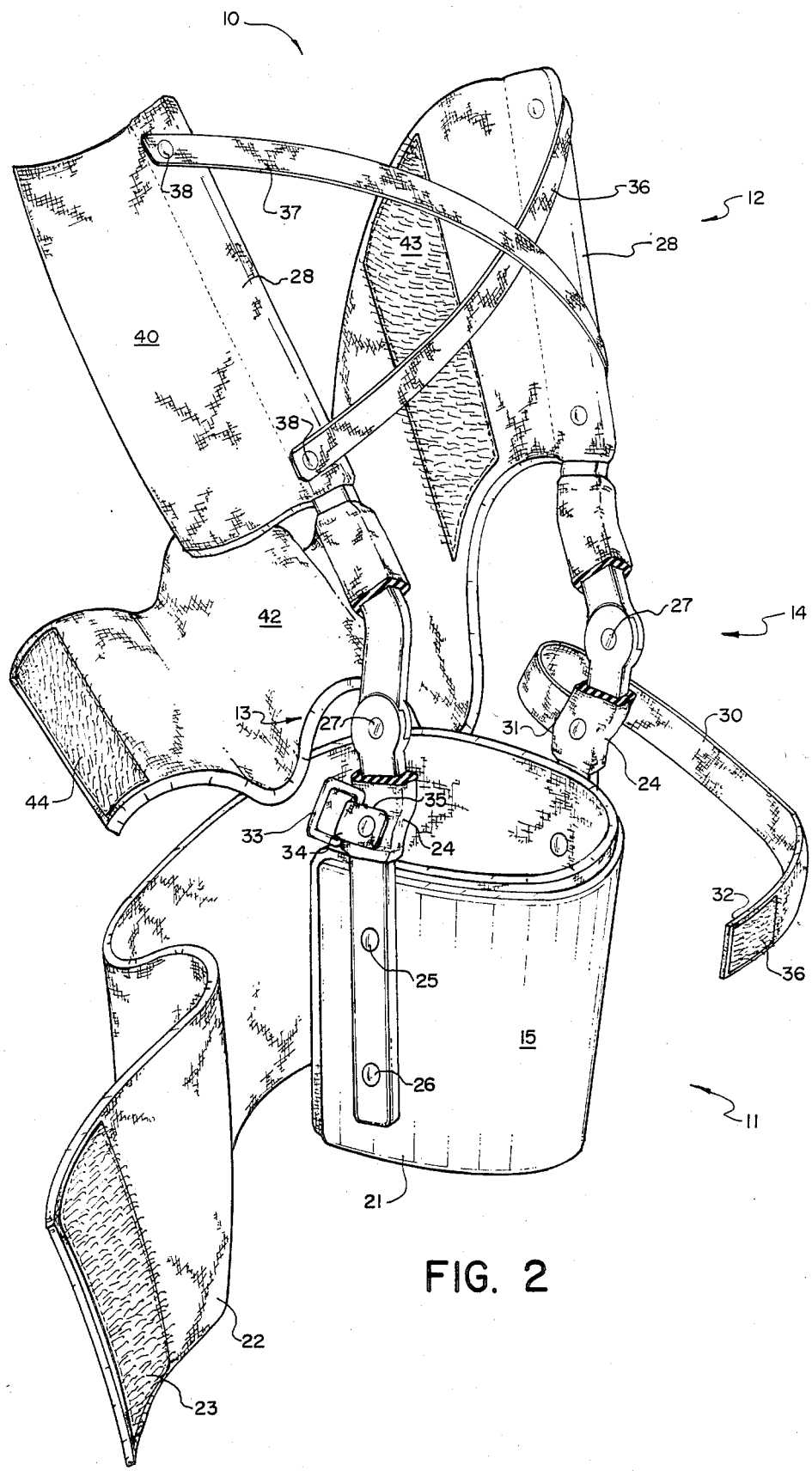

In using the knee brace 10 of the invention the lower cuff is positioned to have the padded shell 15 fit the lower leg and is strapped thereto with strap 30 so that the shell becomes locked to the leg over the tibia. Strap 30 is secured around the leg and the straps 36 and 37 are placed on the upper leg, with the knee-cap between the upper and lower cuffs. The hinges are then on opposite sides of the legs as best shown in FIG. 3. The hinges 14 are angled from the lower cuff to fit closely alongside the leg of the user.

While wearing the knee brace a user can fully bend the knee. During such bending action the crossed straps 36 and 37 permit sufficient movement of the upper portion of the brace with the thigh to accomodate the bending of the knee about plural pivot points as the knee bends in the usual fashion. Consequently, pistoning of the upper and lower cuffs does not occur during use.

The hinges 13 and 14 are preferably covered, above the lower cuff, by a resilient cushion material for the comfort of the user.

Although a preferred form of my invention has been herein disclosed, it is to be understood that the present disclosure is by way of example and that variations are possible without departing from the subject matter coming within the scope of the following claims, which subject matter I regard as my invention.

I cliam:

1. A knee brace comprising
   a lower cuff having a rigid shell molded to fit snugly on the anterior lower leg of a user and strap means extending fully around the shell and the lower leg, said strap means being adapted to rigidly connect the shell to the lower leg of a user;
   an upper cuff including a pair of crossing, flexible, fabric non-resilient straps and spaced upper extension arms comprising components of hinges, and second strap means attached to one of the upper extension arms and adapted to extend around the upper leg of a user and over the crossed straps; and
   hinges including the upper extension arms, interconnecting the lower and upper cuffs, said hinges including lower extension arms rigidly connected to opposite sides of the shell.

2. A knee brace as in claim 1, further including
   a strap connected to one lower extension arm above the shell and means for adjustably connecting the strap snugly across the posterior aspect of the leg above the calf muscle and below the popileteal space of the user.

3. A knee brace as in claim 2, further including
   a protective flap secured to one of the upper extension arms and adapted to extend posteriorly across the thigh.

4. A knee brace as in claim 3, wherein the second strap means has means thereon for releasably locking said strap means to the protective flap.

5. A knee brace as in claim 4, wherein the second strap means fully covers the inside of the shell to provide cushion means therein.

6. A knee brace as in claim 5, wherein the second strap means is of sufficient length to pass fully around the shell and a free end thereof has means to lock the said free end to the second strap intermediate its length.

* * * * *